United States Patent [19]

Acker et al.

[11] 4,330,535

[45] May 18, 1982

[54] FUNGICIDAL AZOLYL-SILYL-GLYCOL ETHERS, THEIR USE FOR COMBATING FUNGI, AND AGENTS THEREFOR

[75] Inventors: Rolf-Dieter Acker, Leimen; Ernst Buschmann, Ludwigshafen; Sabine Thym, Dossenheim; Bernd Zeeh, Ludwigshafen; Ernst-Heinrich Pommer, Limburgerhof, all of Fed. Rep. of Germany

[73] Assignee: BASF Aktiengesellschaft, Fed. Rep. of Germany

[21] Appl. No.: 213,791

[22] Filed: Dec. 8, 1980

[30] Foreign Application Priority Data

Jan. 4, 1980 [DE] Fed. Rep. of Germany ....... 3000140

[51] Int. Cl.$^3$ .......................... A01N 55/02; C07F 7/18
[52] U.S. Cl. .................................... 424/184; 548/110;
[58] Field of Search ........................................ 548/110
424/184

[56] References Cited

U.S. PATENT DOCUMENTS

| | | | |
|---|---|---|---|
| 4,150,122 | 4/1979 | Sauers | 424/184 |
| 4,203,995 | 5/1980 | Funaki et al. | 424/273 R |

FOREIGN PATENT DOCUMENTS 2208329  9/1972  Fed. Rep. of Germany .
2720868 11/1978 Fed. Rep. of Germany .
2758784  7/1979  Fed. Rep. of Germany .
2801579  7/1979  Fed. Rep. of Germany .

OTHER PUBLICATIONS

Birkofer et al., Chem. Ber., 1960, vol. 93, pp. 2804–2809.

*Primary Examiner*—Henry R. Jiles
*Assistant Examiner*—Natalia Harkaway
*Attorney, Agent, or Firm*—Keil & Witherspoon

[57] ABSTRACT

Azolyl-silyl-glycol ethers of the formula

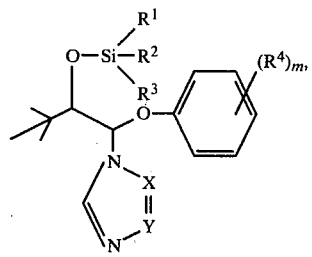

where $R^1$, $R^2$ and $R^3$ denote $C_{1-4}$-alkyl or phenyl, $R^4$ denotes $C_{1-4}$-alkyl, halogen or phenyl, m denotes one of the integers 0, 1, 2 and 3, and X and Y denote CH or N, salts thereof which are tolerated by plants, their manufacture, and their use as fungicides.

9 Claims, No Drawings

FUNGICIDAL AZOLYL-SILYL-GLYCOL ETHERS, THEIR USE FOR COMBATING FUNGI, AND AGENTS THEREFOR

The present invention relates to novel azolyl-silyl-glycol ethers, processes for their manufacture, their use as fungicides, fungicidal agents containing these active ingredients, processes for the manufacture of such fungicidal compositions, and processes for combating injurious fungi with these fungicides or fungicidal compositions containing these compounds.

A fairly large number of biologically active silicon-containing compounds has already been disclosed. The use thereof has up to now been mainly restricted to the field of pharmacology (Journ. of Pharmaceutical Sciences, 60, 1113–1127, 1971, Duetsche Apotheker-Zeitung, 118, 1743–1747, 1978). Little has been published on the use of Si-organic compounds in crop protection (U.S. Pat. No. 4,150,122, German Laid-Open Application DE-OS No. 2,208,329). Nothing has hitherto been disclosed on the use of compounds from this class as fungicides.

We have now found that azolyl-silyl-glycol ethers of the formula

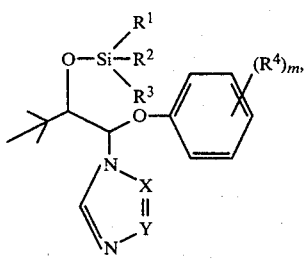

where $R^1$, $R^2$ and $R^3$ denote $C_{1-4}$-alkyl or phenyl, $R^4$ denotes $C_{1-4}$-alkyl, halogen or phenyl, m denotes one of the integers 0, 1, 2 and 3, and X and Y denote CH or N, and salts thereof which are tolerated by plants, have an excellent fungicidal action.

Preferred meanings for $R^1$, $R^2$ and $R^3$, which may be identical or different, are methyl, ethyl and n-butyl.

$R^4$ is preferably chlorine in the 2- and/or 4-position of the phenyl ring; m particularly denotes 1 or 2.

X and Y may be identical or different. Preferably, X is nitrogen and Y a CH group, or X and Y are both CH groups.

The new azolyl-silyl-glycol ethers of the formula I may be prepared by reacting an azolylglycol ether of the formula

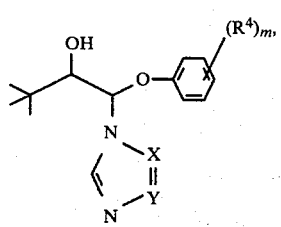

where $R^4$, m, X and Y have the above meanings,
(a) with a trialkylsilyl amide of the formula

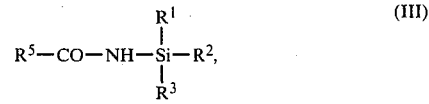

where $R^1$, $R^2$ and $R^3$ have the above meanings and $R^5$ is alkyl or aryl, or (b) —in the presence of an acid-binding agent—with a trialkylchlorosilane of the formula

where $R^1$, $R^2$ and $R^3$ have the above meanings, and the compound thus obtained is converted, if desired, into a salt tolerated by plants.

Advantageously, compounds II are reacted with trialkylsilyl amides III at from 40° to 140° C. in an organic solvent, such as tetrahydrofuran, dioxane, benzene, toluene and xylene.

Examples of suitable silyl amides of the formula III are N-trimethylsilyl acetamide, N-triethylsilyl acetamide, N-(butyl-di-methyl-silyl)-acetamide and N-trimethylsilyl benzamide.

The reaction of II with the trialkylchlorosilanes IV proceeds well at from −5° to +30° C., for instance by dripping the trialkylchlorosilane into a solution of II and the acid neutralizer in a suitable solvent, such as THF, dioxane, $CHCl_3$ or $CH_2Cl_2$. Examples of suitable acid neutralizers are diisopropylethylamine, triethylamine and pyridine. The addition of catalytic amounts of 4-dimethylaminopyridine is advantageous.

Examples of suitable trialkylchlorosilanes IV are trimethylchlorosilane, triethylchlorosilane, n-butyl-dimethylchlorosilane and tert-butyl-dimethylchlorosilane.

Generally, the new compounds are obtained as diastereoisomeric mixtures which may, if desired, be separated by conventional methods.

Although it is generally known that silyl ethers hydrolyze readily under neutral conditions, the azolyl-silyl-glycol ethers I according to the invention are, surprisingly, resistant to hydrolysis. For example, after active ingredient I had been kept for 3 weeks in aqueous methanolic solution, spectroscopy and chromatography revealed no hydrolysis product.

The following examples illustrate the manufacture of compounds I according to the invention.

EXAMPLE 1

1-p-Chlorophenoxy-3,3-dimethyl-2-trimethylsiloxy-1-(1,2,4-triazol-1-yl)-butane

A solution of 10 g of 1-p-chlorophenoxy-3,3-dimethyl-1-(1,2,4-triazol-1-yl)-butan-2-ol and 10 g of N-trimethylsilyl acetamide in 100 ml of anhydrous toluene is heated at 100° C. for 6 hours. If thin-layer chromatography still reveals the presence of starting compound after this period, a further 5 g of N-trimethylsilyl acetamide is added and heating carried out for a further 3 hours at 100° C. The mixture is allowed to cool, a further 400 ml of toluene is added, and the resultant mixture is washed 3 times with 250 ml of $H_2O$, dried over $Na_2SO_4$ and concentrated. The product which remains is subjected to NMR (δ values, $CDCl_3$), which reveals 2 diastereoisomers 1a and 1b of 1-p-chlorophenoxy-3,3-dimethyl-2-trimethylsiloxy-1-(1,2,4-triazol-1-yl)-butane.

1a: $\delta$=0.01 (s, 9H) SiC(CH$_3$)$_3$; 0.96 (s, 9H) C(CH$_3$)$_3$; 3.85 (d, I=5 Hz, 1H), 1h) CHO; 6.10 (d, I=5 Hz, 1H) NCHO;
6.63–7.25 (4H) aromatic; 7.92 (s, 1H); 8.12 (s, 1H) triazole.

1b: $\delta$=0.25 (s, 9H), 0.75 (s, 9H); 3.92 (d, I=3 Hz, 1H); 6.22 (d, I=3 Hz, 1H); 6.63–7.25 (4H); 7.92 (s, 1H), 8.37 (s, 1H).

EXAMPLE 2

1-p-Bromophenoxy-3,3-dimethyl-2-trimethyl-siloxy-1-(1,2,4-triazol-1-yl)-butane

At 0° C., a solution of 8.5 g of trimethylchlorosilane in 20 ml of THF is dripped into a solution of 3.4 g of 1-p-bromophenoxy-3,3-dimethyl-1-(1,2,4-triazol-1-yl)-butan-2-ol and 1.5 g of triethylamine in 40 ml of tetrahydrofuran. The mixture is stirred overnight at room temperature and evaporated, and the residue is taken up in CHCl$_3$, washed several times with water and dried over Na$_2$SO$_4$. After evaporation, the crude product is chromatographed (SiO$_2$, CHCl$_3$). There is obtained 2 g of 1-p-bromophenoxy-3,3-dimethyl-2-trimethylsiloxy-1-(1,2,4-triazol-1-yl)-butane as a colorless resin.

The NMR spectrum shows 2 diastereoisomers:

2a: $\delta$=0.05 (s, 9H), Si(CH$_3$)$_3$; 1.05 (s, 9H) C(CH$_3$)$_3$; 8.0 (s, 1H),
8,50 (s, 1H) (triazole).

2b: $\delta$=0.35 (s, 9H) Si(CH$_3$)$_3$; 0.82 (s, 9H) C(CH$_3$)$_3$; 8.07 (s, 1H);
8.28 (s, 1H) triazole).

EXAMPLE 3

1-p-Phenylphenoxy-3,3-dimethyl-2-triethylsiloxy-1-(1,2,4-triazol-1-yl)-butane 5.5 g of 1-p-phenylphenoxy-3,3-dimethyl-1-(1,2,4-triazol-1-yl)-butan-2-ol is dissolved in 25 ml of THF. 2.9 g of triethylchlorosilane and 0.2 g of 4-dimethylaminopyridine are added under a nitrogen blanket. The mixture is heated to 45° C., and 3.3 g of triethylamine is added in portions. After the mixture has been stirred for 14 hours at from 40° to 50° C. it is cooled to room temperature, undissolved matter is filtered off, and the filtrate is concentrated. The product is further purified either by adding petroleum ether, followed by filtration and concentration, or by gel filtration (SiO$_2$, CHCl$_3$). There is obtained 3 g of 1-p-phenylphenoxy-3,3-dimethyl-2-triethylsiloxy-1-(1,2,4-triazol-1-yl)-butane.

The following compounds were prepared analogously to Examples 1 to 3:

| Ex. no. | R$^1$ | R$^2$ | R$^3$ | (R$^4$)$_m$ | X | Y | $\delta$-values NMR (CDCl$_3$) SiR$^1$R$^2$R$^3$ | C(CH$_3$)$_3$ |
|---|---|---|---|---|---|---|---|---|
| 4 | CH$_3$ | CH$_3$ | CH$_3$ | 2,4-Cl$_2$ | N | CH | 0.01; 0.25 | 0.75; 0.87 |
| 5 | CH$_3$ | CH$_3$ | CH$_3$ | 4-C$_6$H$_5$ | N | CH | 0.0; 0.28 | 0.79; 0.98 |
| 6 | CH$_3$ | CH$_3$ | CH$_3$ | 4-Cl | CH | CH | 0.03; 0.13 | 0.71; 0.73 |
| 7 | CH$_3$ | CH$_3$ | CH$_3$ | 2,4-Cl$_2$ | CH | CH | 0.21 | 0.8 |
| 8 | CH$_3$ | CH$_3$ | CH$_3$ | 2-Cl | CH | N | 0.1 | 0.87 |
| 9 | C$_2$H$_5$ | C$_2$H$_5$ | C$_2$H$_5$ | 4-Cl | N | CH | 0.3–1.1 | 0.99 |
| 10 | C$_2$H$_5$ | C$_2$H$_5$ | C$_2$H$_5$ | 4-Br | N | CH | 0.4–1.2 | 0.89; 0.95 |
| 11 | C$_2$H$_5$ | C$_2$H$_5$ | C$_2$H$_5$ | 2,4-Cl$_2$ | N | CH | 0.3–1.2 | 0.92; 0.95 |
| 12 | CH$_3$ | CH$_3$ | nC$_4$H$_9$ | 4-Cl | N | CH | 0.01; 0.3 0.0–1.4 | 0.77; 1.0 |
| 13 | CH$_3$ | CH$_3$ | nC$_4$H$_9$ | 4-Br | N | CH | 0.01–0.3 0.0–1.5 | 0.78; 1.0 |
| 14 | CH$_3$ | CH$_3$ | nC$_4$H$_9$ | 4-C$_6$H$_5$ | N | CH | 0.0;0.3–1.5 | 1.0 |
| 15 | CH$_3$ | CH$_3$ | nC$_4$H$_9$ | 2,4-Cl$_2$ | N | CH | 0.01; 0.33; 0.0–1.5 | 0.79; 0.90 |
| 16 | CH$_3$ | CH$_3$ | CH$_3$ | 4-CH$_3$ | N | CH | | |
| 17 | CH$_3$ | CH$_3$ | C$_6$H$_5$ | 4-C$_6$H$_5$ | N | CH | | |
| 18 | CH$_3$ | CH$_3$ | t-C$_4$H$_9$ | 4-Cl | N | CH | 0.10; 0.90; | 1.05 |
| 19 | CH$_3$ | CH$_3$ | C$_6$H$_5$ | 4-Cl | N | CH | | |
| 20 | CH$_3$ | CH$_3$ | C$_6$H$_5$ | 4-C$_6$H$_5$ | N | CH | 0.20; 0.25 7.0–7.4 | 0.90 |
| 21 | CH$_3$ | CH$_3$ | C$_6$H$_5$ | 2,4-Cl$_2$ | N | CH | | |
| 22 | CH$_3$ | CH$_3$ | C$_6$H$_5$ | 4-Br | N | CH | | |

The compounds according to the invention and their salts have an excellent action on a board spectrum of plant-pathogenic fungi, particularly from the Ascomycetes and Basidiomycetes classes. Some of them have a systemic action and may be used as foliar and soil fungicides.

The fungicides according to the invention are of particular interest for combatting numerous fungi in various crop plants or their seed, particularly wheat, rye, barley, oats, rice, Indian corn, cotton, soybeans, coffee, sugarcane, fruit and ornamentals in horticulture, and vegetables such as cucumbers, beans and Cucurbitaceae.

The new compounds are especially suitable for combatting the following diseases: *Erysiphe graminis* in cereals, *Erysiphe cichoriacearum* in Cucurbitaceae, *Podosphaera leucotricha* in apples, *Uncinula nector* in grapes, *Erysiphe polygoni* in beans, *Sphaerotheca pannosa* in roses, *Puccinia species* in cereals, *Rhizoctonia solani* in cotton, *Helminthosporium species* in cereals, *Ustilago species* in cereals and sugarcane. *Rhynchosporium secale* in cereals, *Venturia inaequalis* in apples, *Hemileia vastatrix* in coffee, and *Mycosphaerella musicola* in bananas.

The compounds are applied by spraying or dusting the plants with the active ingredients, or by treating the seed with the active ingredients. The compounds may be applied before or after infection of the plants or the seed by fungi.

The compounds according to the invention are very easy to formulate and are extremely stable. The can be converted into the conventional formulations, e.g. solutions, emulsions, suspensions, dusts, powders, pastes and granules. The form of application depends entirely on the purpose for which the agents are being used; it should, however, ensure a fine and uniform distribution of the active ingredient. The formulations are prepared in the conventional manner, for example by diluting the active ingredient with solvents and/or carriers, with or without the addition of emulsifiers and dispersants and, where water is used as the diluent, with or without an organic auxiliary solvent. Suitable auxiliaries are, essentially, solvents, for example aromatics, e.g. xylene and benzene, chloroaromatics, e.g. chlorobenzene, paraffins, e.g. petroleum fractions, alcohols, e.g. methanol and butanol, amines, e.g. ethanolamine and dimethylformamide, and water; carriers, for example natural rock powders, e.g. kaolin, alumina, talc and chalk, and synthetic rock powders, e.g. highly disperse silica and silicates; emulsifiers, for example non-ionic and anionic emulsifiers, e.g. polyoxyethylene fatty alcohol ethers, alkylsulfonates and arylsulfonates, and dispersants, for example lignin, sulfite waste liquors and methylcellulose.

The fungicidal agents in general contain from 0.1 to 95% by weight of active ingredient, preferably from 0.5 to 90%. The application rate depends on the type of effect desired, and is from 0.03 to 3 kg of active ingredient per hectare or more.

The particle size of the active ingredients in the formulations may influence the fungicidal effectiveness. The fungicidal action of some of the compounds increases with decreasing particle size.

The new compounds may also be used for protecting materials, inter alia for combating wood-destroying fungi such as Coniophora puteanea and Polystictus versicolor; solvent-containing wood preservatives contain from 0.05 to 5 wt% of active ingredient, based on the total weight of the formulation. The agents are applied by treating the wood with them, e.g., impregnation or painting.

The formulations, and the ready-to-use preparations obtained therefrom, e.g., solutions, emulsions, suspensions, powders, dusts, pastes or granules, are applied in conventional manner, e.g. by spraying, atomizing, dusting, treating seed, or watering.

Examples of such formulations are as follows:

I. 90 parts by weight of the compound of Example 1 is mixed with 10 parts by weight of N-methyl-Δ-pyrrolidone. A mixture is obtained which is suitable for application in the form of very fine drops.

II. 20 parts by weight of the compound of Example 2 is dissolved in a mixture consisting of 80 parts by weight of xylene, 10 parts by weight of the adduct of 8 to 10 moles of ethylene oxide with 1 mole of oleic acid-N-monoethanolamide, 5 parts by weight of the calcium salt of dodecylbenzenesulfonic acid, and 5 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

III. 20 parts by weight of the compound of Example 3 is dissolved in a mixture consisting of 40 parts by weight of cyclohexanone, 30 parts by weight of isobutanol, 20 parts by weight of the adduct of 7 moles of ethylene oxide with 1 mole of isooctylphenol, and 10 parts by weight of the adduct of 40 moles of ethylene oxide with 1 mole of castor oil. By pouring the solution into 100,000 parts by weight of water and finely distributing it therein, an aqueous dispersion is obtained containing 0.02% by weight of the active ingredient.

IV. 20 parts by weight of the compound of Example 4 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

V. 20 parts by weight of the compound of Example 7 is well mixed with 3 parts by weight of the sodium salt of diisobutylnaphthalene-α-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of the compound of Example 2 is intimately mixed with 97 parts by weight of particulate kaolin. A dust is obtained containing 3% by weight of the active ingredient.

VII. 30 parts by weight of the compound of Example 1 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of the compound of Example 3 is intimately mixed with 10 parts of the sodium salt of a phenolsulfonic acid-urea-formaldehyde condensate, 2 parts of silica gel and 48 parts of water to give a stable, aqueous dispersion. Dilution in 100,000 parts by weight of water gives an aqueous dispersion containing 0.04 wt% of active ingredient.

IX. 20 parts of the compound of Example 4 is intimately mixed with 2 parts of the calcium salt of dodecylbenzenesulfonic acid, 8 parts of a fatty alcohol polyglycol ether, 2 parts of the sodium salt of a phenosulfonic acid-urea-formaldehyde condensate and 68 parts of a paraffinic mineral oil. A stable oily dispersion is obtained.

The above ready-to-use preparations may contain other active ingredients together with those according to the invention, e.g. herbicides, insecticides, growth regulators and other fungicides or may be mixed with fertilizers and applied together with these. Mixture with other fungicides often broadens the spectrum of fungicidal action. The following list of fungicides with which the compounds according to the invention may be combined is intended to illustrate and not restrict the combination possibilities. Examples of fungicides which can be combined with the compounds according to the invention are: dithiocarbamates and their derivatives, e.g. iron (III) dimethyldithiocarbamate, zinc dimethyldithiocarbamate, manganese N,N-ethylene-bis-dithiocarbamate, manganese zinc N,N-ethylenediamine-bis-dithiocarbamate, zinc N,N-ethylene-bis-dithiocarbamate, tetramethylthiuram disulfide, the ammonia complex of zinc N,N-ethylene-bis-dithiocarbamate and N,N'-polyethylene-bis-(thiocarbamoyl)-disulfide, zinc N,N'-propylene-bis-dithiocarbamate, and the ammonia complex of zinc N,N'-propylene-bis-dithiocarbamate and N-N'-polypropylene-bis-(thiocarbamoyl)-disulfide; nitro derivatives, e.g. dinitro-(1-methylheptyl)-phenyl crotonate, 2-sec.-butyl-4,6-dinitrophenyl-3,3-dimethylacrylate and 2-sec.-butyl-4,6-dinitrophenyl isopropyl carbonate; heterocyclic compounds, e.g. N-(1,1,2,2-tetrachloroethylthio)-tetrahydrophthalimide, N-trichloromethylthiotetrahydrophthalimide, N-trichloromethylthio-phthalimide, 2-heptadecyl-2-imidazoline acetate, 2,4-dichloro-6-(o-chloroanilino)-s-triazine, 0,0-diethyl phthalimidophosphonothioate, 5-amino-1-bis-(dimethylamino)-phosphinyl)-3-phenyl-1,2,4-triazole, 5-ethoxy-3-trichloromethyl-1,2,4-thiadiazole, 2,3-dicyano-1,4-dithiaanthraquinone, 2-thio-1,3-dithio-(4,5-b)-quinoxaline, methyl 1-(butylcarbamoyl)-2-benzimidazole-carbamate, 2-methoxycarbonylamino-benzimidazole, 2-thiocyanatomethylthio-benzthiazole, 4-(2-chlorophenylhydrazono)-3-methyl-5-isoxazolone, pyridine-2-thio-1-oxide, 8-hydroxyquinoline and its copper salts, 2,3-dihydro-5-carboxanilido-6-methyl-1,4-oxathiine-4,4-dioxide, 2,3-dihydro-5-carboxanilido-6-methyl-1,4-oxathiine, 2-fur-2-yl-benzimidazole, piperazine-1,4-diyl-bis-(1-(2,2,2-trichloroethyl)-formamide), 2-thiazol-4-yl-benzimidazole, 5-butyl-2-dimethylamino-4-hydroxy-6-methyl-pyrimidine, bis-(p-chlorophenyl)-3-pyridinemethanol, 1,2-bis-(3-ethoxycarbonyl-2-thioureido)-benzene, 1,2-bis-(3-methoxycarbonyl-2-thioureido)-benzene and various fungicides, e.g. dodecylguanidine acetate, 3-(2-(3,5-dimethyl-2-hydroxycyclohexyl)-2-hydroxyethyl)-glutarimide, hexachlorobenzene, N-dichlorofluoromethylthio-N',N'-dimethyl-N-phenyl-sulfuric acid diamide, 2,5-dimethyl-furan-3-carboxylic acid anilide, 2,5-dimethylfuran-3-carboxylic acid cyclohexylamide, 2-cyano-N-(ethylaminocarbonyl)-2-(methoxyimino)-acetamide, 2-methyl-benzoic acid anilide, 2-iodo-benzoic acid anilide, 1-(3,4-dichloroanilino)-1-formylamino-2,2,2-trichloroethane, 2,6-dimethyl-N-tridecyl-morpholine and its salts, 2,6-dimethyl-N-cyclododecyl-morpholine and its salts, D,L-methyl-N-methyl-N-(2,6-dimethylphenyl)-N-fur-2-oyl-alanate, D,L-methyl-N-(2,6-dimethylphenyl)-N-(2'-methoxyacetyl)-alanate, diisopropyl N-nitroisophthalate, 1-(1', 2',4'-triazol-1'-yl)-1-(4'-chlorophenoxy)-3,3-dimethylbutan-2-one, 1-(1',2',4'-triazol-1'-yl)-1-(4'-chlorophenoxy)-3,3-dimethylbutan-2-ol, N-(2,6-dimethylphenyl)-N-chloroacetyl-D,L-2-aminobutyrolactone, and N-(n-propyl)-N-(2,4,6-trichlorophenoxyethyl)-N'-imidazolylurea.

The following Examples A and B demonstrate the biological action of the new compounds. The compound employed for comparison purposes was 1-[2'-(2'',4''-dichlorophenyl)-2'-(2'''-propenyloxy)-ethyl]-1H-imidazole disclosed in German Laid-Open Application DE-OS No. 2,063,857.

EXAMPLE A

Leaves of wheat seedlings of the "Jubilar" variety grown in pots are sprayed with aqueous emulsions prepared from (dry basis) 80% (wt%) active ingredients and 20% emulsifier, and dusted, after the sprayed-on layer has dried, with spores of wheat mildew (*Erysiphe graminis var. tritici*). The plants are then placed in a greenhouse at from 20° to 22° C. and from 75 to 80% relative humidity. The extent of fungus spread is assessed after 10 days.

| Compound of Ex. no. | Leaf attack after spraying with liquor containing compound in amounts of | | |
|---|---|---|---|
| | 0.025% | 0.006% | 0.0015% |
| 1 | 0 | 0 | 0 |
| 2 | 0 | 0 | 0 |
| 4 | 0 | 0 | 0 |
| 5 | 0 | 0 | 1 |
| 6 | 0 | 0 | 0 |
| 7 | 0 | 0 | 0 |
| 8 | 0 | 1 | 1 |
| Comparative agent | 2 | 4 | 5 |
| Control (untreated) | 5 | | |

0 = no fungus attack, graduated down to
5 = total attack

EXAMPLE B

Leaves of pot-grown wheat seedlings of the "Caribo" variety are dusted with spores of leaf rust (*Puccini recondita*). The pots are then placed in a high humidity (90-95%) chamber at from 20° to 22° C. for 24 hours. During this time, the spores germinate and the germ tubes penetrate into the leaf tissue. The infected plants are then sprayed to run-off with aqueous liquors, the solids comprising 80% of active ingredient and 20% of ligninsulfonate. After the spray coating has dried, the test plants are set up in a greenhouse at from 20° to 22° C. and from 65 to 70% relative humidity. After 8 days, the degree of development of the rust fungi on the leaves is determined.

| Compound from Ex. no. | Infection of the leaves after spraying with liquor containing . . .% of active ingredient | | |
|---|---|---|---|
| | 0.025 | 0.006 | 0.0015 |
| 1 | 0 | 0 | 3 |
| 2 | 0 | 1 | 2 |
| 4 | 0 | 2 | 4 |
| 5 | 0 | 0 | 0 |
| 6 | 0 | 2 | 2 |
| 7 | 0 | 2 | 2 |
| Comparative agent | 3 | 5 | 5 |
| Control (untreated) | 5 | | |

0 = no fungus attack, graduated down to
5 = total attack.

We claim:
1. An azolyl-silyl-glycol ether of the formula

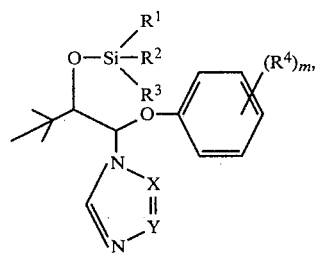

where $R^1$, $R^2$ and $R^3$ denote $C_{1-4}$-alkyl or phenyl, $R^4$ denotes $C_{1-4}$-alkyl, halogen or phenyl, m denotes one of the integers 0, 1, 2 and 3, and X and Y denote CH or N or an organic agriculturally acceptable salt thereof.

2. A compound as claimed in claim 1, wherein X is a nitrogen atom and Y is a CH group.

3. A compound as claimed in claim 1, wherein both X and Y denote CH groups.

4. An azolyl-silyl-glycol ether is claimed in claim 1, selected from the group consisting of 1-p-chlorophenoxy-3,3-dimethyl-2-trimethylsiloxy-1-(1,2,4-triazol-1-yl)-butane, 1-(2,4-dichlorophenoxy)-3,3-dimethyl-2-trimethylsiloxy-1-(1,2,4-triazol-1-yl)-butane and 3,3-dimethyl-2-trimethylsiloxy-1-(4-phenylphenoxy)-1-(1,2,4-triazol-1-yl)-butane.

5. A fungicidal agent comprising a fungicidally effective amount of at least one compound as claimed in any one of claims 1 to 4 and a solid or liquid carrier.

6. A compound as claimed in any one of claims 1 to 4 in the form of an agriculturally acceptable salt thereof.

7. A method for combatting fungi, which comprises applying to a host for fungi growth or the fungi growing thereon a fungicidally effective amount of an azolyl-silyl-glycol ether as claimed in claim 1, or an agriculturally acceptable salt thereof.

8. A method as claimed in claim 7 wherein said ether is in the form of a salt whose fungicidally effective amount is tolerable by agricultural plants.

9. A method for the prophylactic control of growth of fungi, which comprises applying a fungicidally effective amount of an azolyl-silyl-glycol ether as claimed in claim 1, or an agriculturally acceptable salt thereof, to agricultural plants, seeds thereof or other hosts for fungal growth to prevent the growth of fungi on said plants, seeds or other hosts.

* * * * *